(12) United States Patent
Nahtigal

(10) Patent No.: US 10,238,706 B1
(45) Date of Patent: Mar. 26, 2019

(54) CONDENSIBLE GAS BOTANICAL EXTRACTION SYSTEMS AND METHODS

(71) Applicant: MedReleaf Corp., Toronto (CA)

(72) Inventor: Istok Gorazd Nahtigal, Odessa (CA)

(73) Assignee: MedReleaf Corp., Toronto, Ontario (CA)

( * ) Notice: Subject to any disclaimer, the term of this patent is extended or adjusted under 35 U.S.C. 154(b) by 0 days.

(21) Appl. No.: 15/842,054

(22) Filed: Dec. 14, 2017

(51) Int. Cl.
| | | |
|---|---|---|
| *A61K 36/00* | (2006.01) | |
| *A61K 36/185* | (2006.01) | |
| *B01D 11/02* | (2006.01) | |
| *A61K 31/352* | (2006.01) | |

(52) U.S. Cl.
CPC .......... *A61K 36/185* (2013.01); *A61K 31/352* (2013.01); *B01D 11/0203* (2013.01); *B01D 11/0215* (2013.01); *A61K 2236/37* (2013.01); *A61K 2236/53* (2013.01)

(58) Field of Classification Search
CPC ...................................................... A61K 36/00
USPC ......................................................... 424/725
See application file for complete search history.

(56) References Cited

U.S. PATENT DOCUMENTS

| | | |
|---|---|---|
| 4,824,570 A | 4/1989 | Bethuel et al. |
| 8,025,797 B2 | 9/2011 | Hsieh |
| 8,048,304 B2 | 11/2011 | Waibel et al. |
| 8,829,214 B2 | 9/2014 | Ismail et al. |
| 2008/0233238 A1 | 9/2008 | Roney et al. |
| 2010/0221397 A1 | 9/2010 | Iversen et al. |
| 2012/0046351 A1* | 2/2012 | Hospodor ............... A23G 1/42 514/454 |
| 2016/0279535 A1 | 9/2016 | Jones |
| 2017/0015937 A1 | 1/2017 | Kinney et al. |

FOREIGN PATENT DOCUMENTS

WO 2016161420 A1 10/2016

\* cited by examiner

*Primary Examiner* — Michael V Meller
(74) *Attorney, Agent, or Firm* — Philip C. Mendes da Costa; Bereskin & Parr LLP, S.E.N.C.R.L, s.r.l.

(57) ABSTRACT

An apparatus for the extraction of compounds from botanical material using a condensable gas solvent includes an extraction chamber wherein the feedstock is extracted while in a frozen state.

14 Claims, 9 Drawing Sheets

CONDENSIBLE GAS BOTANICAL EXTRACTION SYSTEMS AND METHODS

FIELD

This disclosure relates generally to apparatus and methods for the extraction of compounds from botanical material using a condensable gas solvent. More specifically, this disclosure relates to apparatus and methods for the extraction of compounds from *cannabis*, such as aliphatic aldehydes, monoterpenes, and cannabinoids.

INTRODUCTION

The following is not an admission that anything discussed below is part of the prior art or part of the common general knowledge of a person skilled in the art.

Botanicals extracts are a growing product class in the *cannabis* industry. Advantageously, extracts may have some or all of the benefits of the original plant, in a convenient concentrated form.

Popular methods used to extract various compounds from botanicals involve the use of solvents, typically alcohol or water (often in the form of steam). These solvents diffuse the plant material and draw out one or more plant compounds. More often than not, the solvent is removed from the final extract. In order to extract the more hydrophobic compounds, hydrocarbon or chlorinated solvents may be used, subsequently leaving residues that may be challenging to remove or minimize.

SUMMARY

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

Condensable gas solvent may be used to extract one or more compounds from botanical material, such as a *cannabis* feedstock. Advantageously, condensable gases can be liquefied at moderate pressures at ambient temperature. Condensable gas solvents may also for be used for extraction at relatively wide temperature and pressure range. This may enable improved solubility performance, and/or provide a more complete extraction in less time when compared to other solvents.

In particular, carbon dioxide ($CO_2$) is considered to be a preferred solvent for *cannabis* extraction. For example, it is regarded as non-toxic, environmentally friendly, relatively inexpensive, and leaves no residue when the extracted compounds are separated from the solvent. Also, the low viscosity of supercritical carbon dioxide may allow it to penetrate into botanical material more easily, while its diffusivity may allow for faster extractions.

In accordance with one aspect of this disclosure, which may be used alone or in combination with one or more other aspects, apparatus for the extraction of compounds from botanical material using a condensable gas solvent includes using a sonic flow nozzle that is positioned adjacent a cyclone chamber to introduce a mixture of a solvent and a botanical extract into a cyclone chamber. The sonic flow nozzle may be proximate (e.g., immediately upstream of) a tangential fluid inlet of the cyclone chamber or a tangential inlet may comprise or consist of a sonic flow nozzle.

According to this aspect, the feed to a cyclone separator (e.g., a compressible gas solvent (e.g. $CO_2$) and a botanical extract dissolved therein) may be accelerated to sonic or supersonic speeds and introduced directly into the cyclone chamber. Accordingly, a solvent containing extracted botanical elements may exit the sonic flow nozzle at a supersonic velocity and be directly tangentially introduced into a cyclone separator. An advantage of this design is that it may promote greater separation efficiency, in that most, substantially all, or essentially all of the extracted material dissolved or contained in the solvent stream may be separated from the gas solvent. For example, more than 85%, 90%, 95%, 96%, 97%, 98%, or 99% of the extracted material dissolved in the solvent stream may be separated from the gas solvent as an unfoamed extract as exemplified in FIG. 9. As a result, gaseous solvent exiting the cyclonic separator may have little or no solute. For example, less than 15%, 10%, 5%, 4%, 3%, 2% or 1% of extracted botanical compound(s) may remain in the gaseous solvent exiting the cyclonic separator. A further advantage is that this may allow 'clean' (i.e. substantially or completely extract-free) solvent to be recycled to an extraction chamber.

This separation efficiency may be contrasted with typical cyclone separator systems which use a typical cyclone inlet wherein there may be significant volumes of solvent in the botanical extract exiting a cyclone separator. For example, the botanical extract exiting a cyclone separator may be in the form of an emulsion or foamed liquid extract which may contain 2% or more solvent (see for example FIG. 8). The downstream processing of such products is difficult as the extract is not easily flowable and may foul the low pressure piping and compression pumps downstream of the separator.

In contrast, in accordance with this aspect, the solvent-extract stream from the extraction chamber may undergo simultaneous depressurization and acceleration immediately upstream of, or as it enters the cyclone chamber, forming liquid droplets of extracted compounds which may flow under the influence of gravity down the wall of a cyclone separator so as to be collected as, e.g., an unfoamed liquid (see for example FIG. 9).

A further advantage of this aspect is that it may allow the sonic flow nozzle to be operated in a 'choked' state. An advantage of operating the flow nozzle under 'choked' conditions is that pressure disturbances upstream of the sonic flow nozzle may be inhibited or prevented from moving downstream into the cyclonic separator, and thus may be inhibited or prevented from causing undesirable pulsations and/or vortex flow instabilities during the decompression and/or separation that occurs in the cyclonic separator.

In accordance with this aspect, there is provided an apparatus for the extraction of compounds from botanical material using a condensable gas solvent, the apparatus comprising:

(a) an extraction chamber having a solvent outlet;

(b) a cyclonic separator comprising a cyclone chamber having a cyclonic tangential fluid inlet and a fluid outlet;

(c) a solvent flow path extending from the solvent outlet of the extraction chamber to the cyclonic tangential fluid inlet; and, (d) a sonic flow nozzle positioned in the solvent flow path adjacent the cyclonic tangential fluid inlet.

In any embodiment, the sonic flow nozzle may be positioned at an upstream end of the cyclonic tangential fluid inlet whereby the solvent passing through the sonic flow nozzle enters the cyclone chamber at sonic velocity.

In any embodiment, the sonic flow nozzle may comprise the cyclonic tangential fluid inlet.

In any embodiment, the extraction chamber may be operated below 0° C. and with the solvent in a liquid or a supercritical phase, and the solvent flow path may further comprise a heater proximate an inlet of the sonic flow nozzle wherein the solvent exiting the heater is gaseous.

In any embodiment, the apparatus may further comprise a solvent return path extending from the fluid outlet of the cyclonic separator to the extraction chamber.

In any embodiment, the outlet of the sonic flow nozzle may be positioned at an inlet port of the cyclone separator.

In accordance with this aspect, there is also provided a method for extracting compounds from botanical material using a condensable gas solvent, the method comprising:

(a) in an extraction chamber, using the condensable gas solvent to extract at least one compound from a feedstock of botanical material;

(b) withdrawing a liquid solvent containing the at least one compound extracted from the feedstock from the extraction chamber and conveying the liquid solvent through a solvent flow path to a sonic flow nozzle and obtaining solvent at a supersonic velocity; and, (c) directly tangentially introducing the solvent exiting the sonic flow nozzle at a supersonic velocity into a cyclone separator.

In any embodiment, the solvent in the flow path may be in a phase comprising at least one of a supercritical phase and a liquid phase.

In any embodiment, the solvent in the extraction chamber may be in a liquid phase and the solvent in the flow path may be in a supercritical phase.

In any embodiment, the method may further comprise heating the solvent to a gaseous phase prior to the solvent entering the sonic flow nozzle.

In any embodiment, the solvent in the extraction chamber may be in a liquid phase and the solvent in the flow path may be in a supercritical phase.

In any embodiment, the method may further comprise separating at least a portion of the at least one compound from the solvent in the cyclone separator and collecting the at least one compound as an unfoamed liquid.

In any embodiment, the method may further comprise heating the cyclone separator whereby the at least one compound that is separated in the cyclone separator may be heated and its viscosity may be reduced.

In any embodiment, the outlet of the sonic flow nozzle may be positioned adjacent the cyclone separator and the method may further comprise directing solvent exiting the sonic flow nozzle to avoid the solvent contacting an inlet port of the cyclone separator.

In any embodiment, the outlet of the sonic flow nozzle may be positioned at an inlet port of the cyclone separator and the method may further comprise conveying solvent exiting the sonic flow nozzle immediately into the cyclone separator.

In any embodiment, the feedstock of botanical material may comprise *cannabis* and the method may further comprise obtaining as the at least one compound extracted from the feedstock at least one of an aliphatic aldehyde, a terpene, and a cannabinoid.

In accordance with another aspect of this disclosure, which may be used alone or in combination with one or more other aspects, a method for extracting compounds from botanical material comprising *cannabis* using a condensable gas solvent includes extracting a compound from the *cannabis* using condensable gas solvent in a liquid and/or supercritical phase. A liquid stream of solvent and the extracted compound is conveyed to a cyclone chamber, and solvent in the liquid stream is converted to a gaseous phase upstream of the cyclone chamber. Solvent in the gaseous phase is then directed into the cyclone chamber at sonic velocity.

An advantage of this aspect is that solvent containing extracted compounds may be maintained in a liquid and/or supercritical phase upstream of the cyclone chamber, which may facilitate maintaining the solvent density at a level sufficient to inhibit or prevent the extracted compounds from being disassociated from the solvent upstream of the cyclone chamber thereby preventing or reducing fouling of the flow path from the extractor to the cyclone separator.

In accordance with this aspect, there is provided a method for extracting compounds from botanical material comprising *cannabis* using a condensable gas solvent, the method comprising:

(a) in an extraction chamber, using the condensable gas solvent in a phase comprising at least one of a supercritical phase and a liquid phase to extract at least one compound from the *cannabis;*

(b) withdrawing a liquid stream comprising the solvent the at least one compound and conveying the liquid stream along a solvent flow path extending from the extraction chamber to a cyclone chamber having a fluid inlet;

(c) converting the solvent in the liquid stream to a gaseous phase upstream of the cyclone chamber; and, (d) directing the solvent in the gaseous phase into the cyclone chamber via the fluid inlet at sonic velocity.

In any embodiment, conveying the liquid stream containing the at least one compound may comprise directing solvent through a sonic flow nozzle positioned in the solvent flow path upstream of the fluid inlet.

In any embodiment, the fluid inlet may comprise the sonic flow nozzle.

In any embodiment, the fluid inlet may be a tangential air inlet.

In any embodiment, the method may further comprise separating at least a portion of the at least one compound from the solvent in the cyclone chamber and collecting the at least one compound as an unfoamed liquid.

In any embodiment, the method may further comprise heating the cyclone chamber whereby the at least one compound that is separated in the cyclone chamber may be heated and its viscosity may be reduced.

In any embodiment, the method may further comprise selecting the condensable gas solvent from at least one of carbon dioxide, a hydrocarbon, preferably a haloalkane, Xenon, nitrous oxide, and sulfur hexafluoride.

In any embodiment, the method may further comprise selecting carbon dioxide as the condensable gas solvent.

In any embodiment, the at least one compound extracted from the feedstock may comprise at least one of an aliphatic aldehyde, a ketone, an ester, a terpene, and a cannabinoid.

In accordance with another aspect of this disclosure, which may be used alone or in combination with one or more other aspects, a method for extracting compounds from botanical material comprising *cannabis* using a condensable gas solvent includes providing a frozen feedstock of botanical material (e.g. all or substantially all of the water in the feedstock is in a solid phase) to an extraction chamber, and extracting a compound from the feedstock using a condensable gas solvent while maintaining the feedstock in a frozen state.

An advantage of extracting compounds from frozen botanical material is that it may impede or prevent water in the botanical material from being dissolved by the solvent. This may result in a more 'complete' extract being obtained, and may also improve the speed and/or efficiency of the solvent extraction. For example, some terpenes are somewhat water soluble. If the recovered extract contains a significant amount of water, then when the water is removed, some of the terpenes may be lost.

Another possible advantage is that this may reduce or obviate the need to desiccate the material prior to extraction. This may be particularly advantageous for extracting compounds from a *cannabis* feedstock. For example, one or more compounds typically present in *cannabis* may be lost, damaged, or otherwise adversely affected during a typical drying process.

In accordance with this broad aspect, there is provided a method for extracting compounds from botanical material comprising *cannabis* using a condensable gas solvent, the method comprising:

(a) providing a feedstock of the botanical material to an extraction chamber wherein water in the feedstock is in a solid phase;

(b) extracting at least one compound from the feedstock of the botanical material using the condensable gas solvent while maintaining the feedstock in a frozen state and obtaining solvent containing the at least one extracted compound;

(c) withdrawing a solvent stream containing the at least one extracted compound from the extraction chamber; and, (d) separating the at least one extracted compound from the solvent stream.

In any embodiment, the feedstock of botanical material provided in the extraction chamber may have a moisture content of at least 9%.

In any embodiment, the feedstock of botanical material provided in the extraction chamber may have a moisture content of at least 12%.

In any embodiment, in step (a) at least 50% of the water in the feedstock may be in the solid phase.

In any embodiment, the method may further comprise controlling process conditions of the extraction chamber such that the solvent in the extraction chamber is in at least one of a liquid phase and a supercritical phase.

In any embodiment, step (d) may comprise separating the at least one extracted compound from the solvent stream in a cyclonic separator.

In any embodiment, in step (a), the feedstock may be introduced into the extraction chamber in an unfrozen state.

In any embodiment, the feedstock of botanical material introduced to the extraction chamber may have a moisture content of at least 5%.

In any embodiment, the solvent in the extraction chamber may be in a liquid phase.

In any embodiment, the method may further comprise obtaining fresh feedstock and step (a) may comprise introducing the fresh feedstock into the extraction chamber.

In any embodiment, the method may further comprise introducing the fresh feedstock having a moisture content of at least 5% into the extraction chamber.

In any embodiment, the solvent in the extraction chamber may be in a liquid phase.

In any embodiment, the at least one compound extracted from the feedstock may comprise at least one of an aliphatic aldehyde, a terpene, and a cannabinoid.

In accordance with another aspect of this disclosure, which may be used alone or in combination with one or more other aspects, a method for extracting compounds from botanical material using a condensable gas solvent includes extracting the botanical material at conditions at which a condensable solvent is in a liquid phase and heating the solvent containing at least one compound extracted from the botanical material in a heating zone located upstream from a cyclone separator. The heating zone may be proximate to or immediately upstream of a cyclone separator. Accordingly, the solvent is heated and conveyed to a cyclone chamber (e.g., a tangential inlet of a cyclone separator, which may comprise or consist of a sonic flow nozzle) at conditions at which the solvent is in a gaseous phase. Accordingly, the solvent may be conveyed to the cyclone inlet as a liquid and converted to a gas upstream or immediately upstream of a sonic flow nozzle or a tangential cyclone inlet.

An advantage of this design is that solvent containing extracted compounds may be heated and brought to an inlet of a flow nozzle in a gaseous phase, which may facilitate maintaining the solvent density at a level sufficient to inhibit or prevent the extracted compounds from being disassociated from the solvent upstream of the flow nozzle, thereby preventing or reducing fouling of the flow path from the extractor to the cyclone separator.

In accordance with this broad aspect, there is provided a method for extracting compounds from botanical material using a condensable gas solvent, the method comprising:

(a) providing a feedstock of botanical material and condensable gas solvent in an extraction chamber at conditions at which the solvent is at least primarily in a liquid phase;

(b) conveying solvent containing at least one compound extracted from the feedstock along a solvent flow path extending from the extraction chamber to a heating zone;

(c) heating the solvent and conveying the solvent from the heating zone to an inlet of a flow nozzle at conditions at which the solvent is at least primarily in a gaseous phase; and, (d) directing the gaseous solvent to a cyclone chamber and operating the cyclone chamber at conditions at which the solvent within the cyclone chamber is primarily in a gas phase and the at least one compound extracted from the feedstock is primarily in a liquid phase.

In any embodiment, the flow nozzle may be a sonic flow nozzle and the method may further comprise obtaining solvent exits the outlet of the flow nozzle at sonic velocity.

In any embodiment, controlling process conditions of the extraction chamber may comprise bringing the temperature of solvent in the extraction chamber to a temperature at or below the freezing point of water, such that at least a portion of water in the feedstock of botanical material is in a solid phase.

In accordance with another aspect of this disclosure, which may be used alone or in combination with one or more other aspects, apparatus for the extraction of compounds from botanical material is provided. The apparatus includes an extraction chamber, and two or more cyclonic separation stages for removing extracted compounds from a solvent stream. At least one valve is operable to selectively direct solvent from the extraction chamber to one of the cyclonic separation stages.

An advantage of this design is that the cyclonic separation stages may each be configured to preferentially separate certain compounds or classes of compounds from a solvent stream. For example, a first cyclonic separator may be configured or 'tuned' to preferentially remove a first series of extracted compounds from a solvent stream, and a second cyclonic separator may be configured or 'tuned' to preferentially remove a second, higher molecular weight, series of extracted compounds from a solvent stream. This may allow a solvent stream containing certain compound(s) to be directed from the extraction chamber to the cyclonic separator best suited to remove those compound(s).

In accordance with this broad aspect, there is provided apparatus for the extraction of compounds from botanical material, the apparatus comprising:

(a) an extraction chamber;

(b) a first cyclonic separation stage comprising at least one first stage cyclonic separator wherein the at least one first stage cyclonic separator is configured to remove a first series of extracted compounds having a first average molecular weight from a solvent stream;

(c) a first solvent flow path extending from the extraction chamber to the first cyclonic separation stage;

(d) a second cyclonic separation stage comprising at least one second stage cyclonic separator wherein the at least one second stage cyclonic separator is configured to remove a second series of extracted compounds from a solvent stream wherein the second series of extracted compounds has a second average molecular weight that is higher than the first average molecular weight;

(e) a second solvent flow path extending from the extraction chamber to the second cyclonic separation stage; and, (f) at least one valve operable to selectively direct solvent exiting the extraction chamber to one of the first cyclonic separation stage and the second cyclonic separation stage.

In any embodiment, the apparatus may further comprise:

a third cyclonic separation stage comprising at least one third stage cyclonic separator wherein the at least one third cyclonic stage separator is configured to remove a third series of extracted compounds from a solvent stream wherein the third series of extracted compounds has a third average molecular weight that is higher than the second average molecular weight; and, a third solvent flow path extending from the extraction chamber to the third cyclonic separation stage, wherein the at least one valve is operable to selectively direct solvent exiting the extraction chamber to one of the first cyclonic separation stage, the second cyclonic separation stage, and the third cyclonic separation stage.

In any embodiment, solvent obtained from the extraction chamber may rotate at a first speed in the at least one first stage cyclonic separator and solvent obtained from the extraction chamber may rotate at a second speed in the at least one second stage cyclonic separator wherein the second speed may be different than the first speed.

In any embodiment, solvent obtained from the extraction chamber may rotate at a first speed in the at least one first stage cyclonic separator, solvent obtained from the extraction chamber may rotate at a second speed in the at least one second stage cyclonic separator wherein the second speed may be different than the first speed, and solvent obtained from the extraction chamber may rotate at a third speed in the at least one third cyclonic separator wherein the third speed may be different than the first speed and the second speed.

In any embodiment, the first solvent flow path may comprise a common solvent flow path portion downstream of the extraction chamber and upstream of the at least one valve and a first segregated solvent flow path portion downstream of the at least one valve and upstream of the first cyclonic separation stage, and wherein the second solvent flow path may comprise the common solvent flow path portion and a second segregated solvent flow path portion downstream of the at least one valve and upstream of the second cyclonic separation stage.

In any embodiment, the first solvent flow path may comprise a common solvent flow path portion downstream of the extraction chamber and upstream of the at least one valve and a first segregated solvent flow path portion downstream of the at least one valve and upstream of the first cyclonic separation stage, and wherein the second solvent flow path may comprise the common solvent flow path portion and a second segregated solvent flow path portion downstream of the at least one valve and upstream of the second cyclonic separation stage, and wherein the third solvent flow path may comprise the common solvent flow path portion and a third segregated solvent flow path portion downstream of the at least one valve and upstream of the third cyclonic separation stage.

In any embodiment, the apparatus may further comprise an extraction control system for regulating at least one of a temperature and a pressure of solvent in the extraction chamber, the extraction control system may be configured to operate the extraction chamber under at least a first set of process conditions and a second set of process of conditions, and wherein, while the extraction chamber is being operated under the first set of process conditions, the at least one valve may be configured to direct solvent exiting the extraction chamber to the first cyclonic separation stage, and wherein, while the extraction chamber is being operated under the second set of process conditions, the at least one valve may be configured to direct solvent exiting the extraction chamber to the second cyclonic separation stage.

In accordance with another aspect of this disclosure, which may be used alone or in combination with one or more other aspects, a method of extracting compounds from botanical material is provided. First, solvent is used under a first set of process conditions to preferentially extract a first compound from a feedstock of botanical material, and solvent containing the first extracted compound is conveyed to a first cyclonic separation stage. Next, solvent is used under a second set of process conditions to preferentially extract a second compound from the feedstock, and solvent containing the second extracted compound is conveyed to a second cyclonic separation stage.

An advantage of using condensable gas as a solvent is that it may allow the preferential extraction (or 'targeted' extraction) of one or more individual compounds from a botanical feedstock. For example, controlling the density of solvent during the extraction process (e.g. by altering the temperature and/or pressure of solvent in a liquid and/or supercritical phase) may promote conditions in which the solubility and/or rate of solution of one or more compounds (e.g., one or more terpenes) present in the botanical material is relatively high in comparison with other compounds (e.g., other terpenes) present in the botanical material. Under such conditions, one or more 'targeted' compound class(es) may be dissolved by the solvent and drawn from the botanical material in disproportionate quantities and/or at a disproportionate rate to other compounds present in the botanical material.

Another advantage of this design is that the cyclonic separation stages may each be configured or 'tuned' to preferentially separate certain compounds from solvent. For example, a first cyclonic separator may be configured to preferentially remove a first 'targeted' extracted compound(s) (e.g., one or more terpenes) from a solvent stream, and a second cyclonic separator may be configured to preferentially remove a second 'targeted' extracted compound(s) (e.g., other terpenes) from the solvent. This may allow solvent containing certain targeted compound(s) to be directed to a cyclonic separator best suited to disassociate those compound(s) from solvent.

In accordance with this aspect, there is provided a method for extracting compounds from botanical material using apparatus comprising an extraction chamber, a first cyclonic separation stage comprising at least one first stage cyclonic separator, and a second cyclonic separation stage comprising at least one second stage cyclonic separator, the method comprising:

(a) introducing a feedstock of botanical material into the extraction chamber;

(b) operating the extraction chamber using a first solvent under a first set of process conditions to preferentially extract a first compound from the feedstock;

(c) conveying the first solvent containing the first extracted compound from the extraction chamber to the first cyclonic separation stage along a first solvent flow path;

(d) separating the first extracted compound from the first solvent in the first cyclonic separation stage;

(e) operating the extraction chamber using a second solvent under a second set of process conditions to preferentially extract a second compound from the feedstock;

(f) conveying the second solvent containing the second extracted compound from the extraction chamber to the second cyclonic separation stage along a second solvent flow path; and, (g) separating the second extracted compound from the second solvent in the second cyclonic separation stage.

In any embodiment, the method may further comprise recycling the first solvent from the first cyclonic separation stage to the extraction chamber.

In any embodiment, the method may further comprise recycling the second solvent from the first cyclonic separation stage to the extraction chamber.

In any embodiment, the second solvent may be selected to be the same as the first solvent.

In accordance with another aspect of this disclosure, which may be used alone or in combination with one or more other aspects, a method for extracting compounds from botanical material using a condensable gas solvent includes conducting sequential extraction operations to sequentially extract heavier molecular weight compounds and conveying the solvent from the extraction operations sequentially though cyclonic separation stages to sequentially obtain recovered extracts having lighter molecular weights.

In accordance with this aspect, there is provided an apparatus for the extraction of compounds from botanical material, the apparatus comprising:

(a) an extraction chamber;

(b) a first cyclonic separation stage comprising at least one first stage cyclonic separator wherein the at least one first stage cyclonic separator is configured to remove a first series of extracted compounds having a first average molecular weight from a solvent stream obtained from the extraction chamber;

(c) a first solvent flow path extending from the extraction chamber to the first cyclonic separation stage;

(d) a second cyclonic separation stage comprising at least one second stage cyclonic separator wherein the at least one second stage cyclonic separator is configured to remove a second series of extracted compounds from a solvent stream obtained from the first cyclonic separation stage wherein the second series of extracted compounds has a second average molecular weight that is lower than the first average molecular weight; and, (e) a second solvent flow path extending from the first cyclonic separation stage to the second cyclonic separation stage.

In any embodiment, the apparatus may further comprise a third cyclonic separation stage comprising at least one third stage cyclonic separator wherein the at least one third cyclonic stage separator is configured to remove a third series of extracted compounds from a solvent stream wherein the third series of extracted compounds has a third average molecular weight that is lighter than the second average molecular weight; and, a third solvent flow path extending from the second cyclonic separation stage to the third cyclonic separation stage.

In any embodiment, the solvent obtained from the extraction chamber may rotate at a first speed in the at least one first stage cyclonic separator and solvent obtained from the extraction chamber may rotate at a second speed in the at least one second stage cyclonic separator wherein the second speed may be higher than the first speed.

In any embodiment, the solvent obtained from the extraction chamber may rotate at a first speed in the at least one first stage cyclonic separator, solvent obtained from the extraction chamber may rotate at a second speed in the at least one second stage cyclonic separator wherein the second speed may be higher than the first speed, and solvent obtained from the extraction chamber may rotate at a third speed in the at least one third cyclonic separator wherein the third speed may be higher than the second speed.

In accordance with this aspect, there is also provided a method for extracting compounds from botanical material using apparatus comprising an extraction chamber, a first cyclonic separation stage comprising at least one first stage cyclonic separator, and a second cyclonic separation stage comprising at least one second stage cyclonic separator, the method comprising:

(a) introducing a feedstock of botanical material into the extraction chamber;

(b) conducting a first extraction operation in which the extraction chamber is operated using a solvent under a first set of process conditions to preferentially extract a first compound from the feedstock;

(c) subsequently conducting a second extraction operation in which the extraction chamber is operated using the solvent under a second set of process conditions to preferentially extract a second compound from the feedstock wherein the second compound has a higher molecular weight than the first compound;

(d) conveying the solvent from each extraction operation to the first cyclonic separation stage and separating the first extracted compound from the solvent in the first cyclonic separation stage; and, (e) conveying partially treated solvent obtained from the first cyclonic separation stage to the second cyclonic separation stage and separating the second extracted compound from the partially treated solvent in the second cyclonic separation stage.

In any embodiment, the method may further comprise obtaining fully extracted solvent from the second cyclonic separation stage and recycling the fully extracted solvent to the extraction chamber.

In any embodiment, the solvent obtained from the extraction chamber may rotate at a first speed in the at least one first stage cyclonic separator and the partially extracted solvent may rotate at a second speed in the at least one second stage cyclonic separator wherein the second speed may be higher than the first speed.

It will be appreciated by a person skilled in the art that an apparatus or method disclosed herein may embody any one or more of the features contained herein and that the features may be used in any particular combination or sub-combination.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which.

Figure 1:
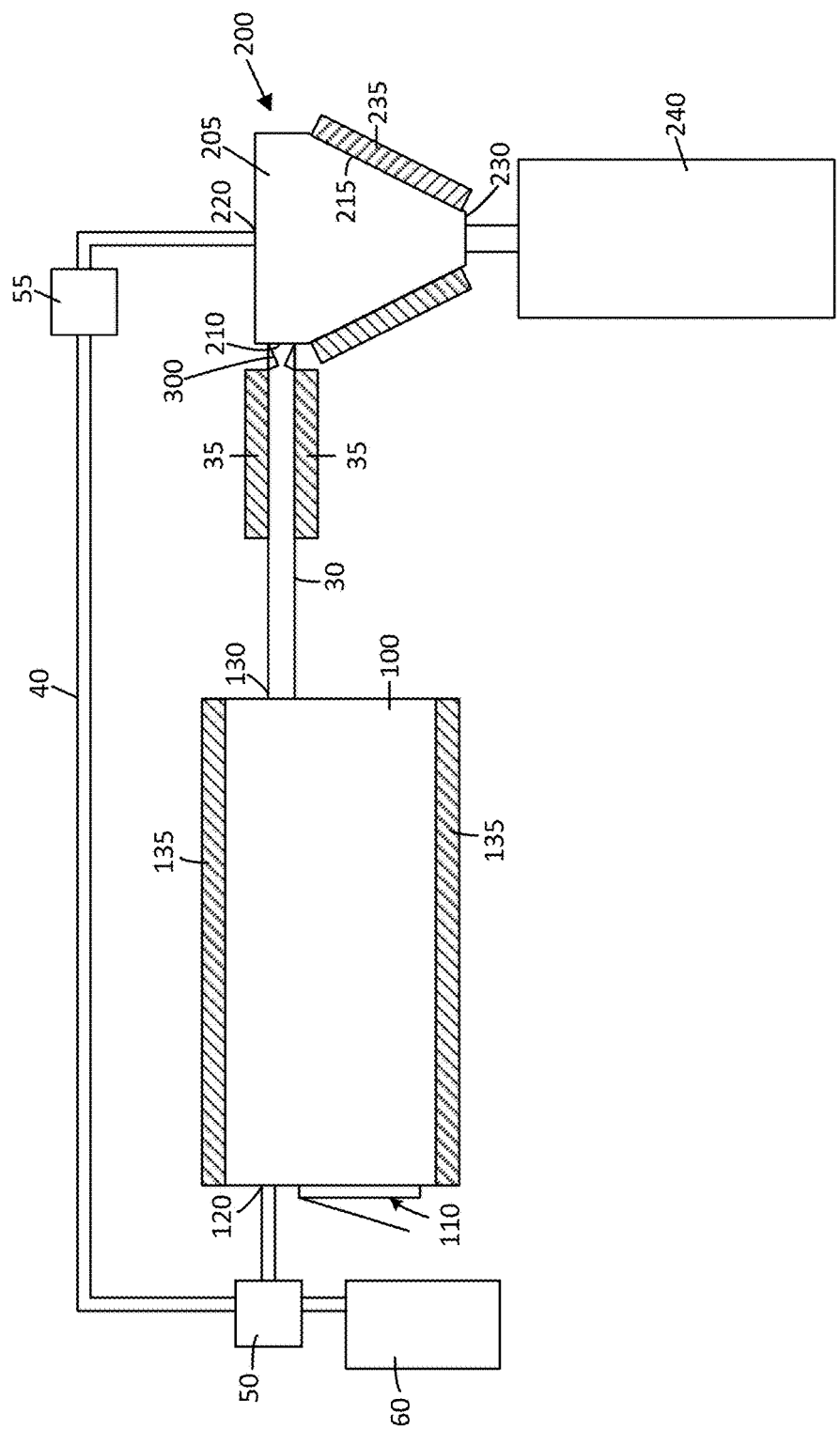
FIG. 1 is a schematic view of an apparatus for the extraction of compounds from a botanical material in accordance with one embodiment.
Figure 2:
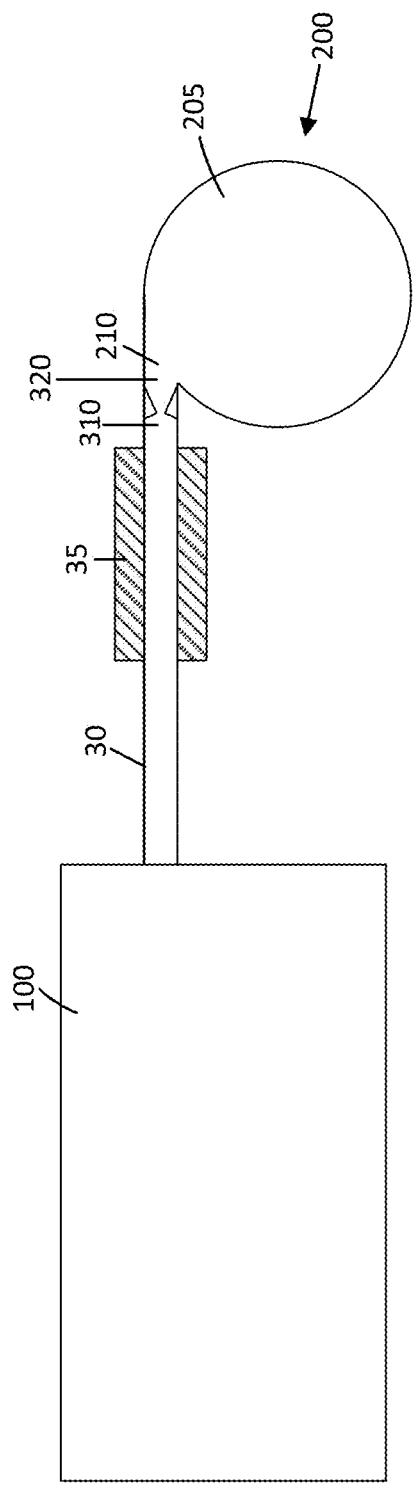
FIG. 2 is a top schematic view of the extraction chamber, solvent flow path, sonic flow nozzle, cyclone chamber, and cyclonic tangential fluid inlet of the apparatus of FIG. 1.

The drawings included herewith are for illustrating various examples of articles, methods, and apparatuses of the teaching of the present specification and are not intended to limit the scope of what is taught in any way.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", or "fastened" where the parts are joined or operate together either directly or indirectly (i.e., through one or more intermediate parts), so long as a link occurs. As used herein and in the claims, two or more parts are said to be "directly coupled", "directly connected", "directly attached", or "directly fastened" where the parts are connected in physical contact with each other. None of the terms "coupled", "connected", "attached", and "fastened" distinguish the manner in which two or more parts are joined together.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

General Description of an Apparatus for the Extraction of Compounds from Botanical Material Referring to FIGS. 1 to 4, an exemplary embodiment of an apparatus for the extraction of compounds from botanical material (which may be referred to as a botanical feedstock and is preferably *cannabis*) is shown generally as 1000. The following is a general discussion of this embodiment which provides a basis for understanding several of the features which are discussed herein. As discussed subsequently, each of the features may be used individually or in any particular combination or sub-combination in this or in other embodiments disclosed herein.

In the illustrated embodiment, the apparatus extracts compounds from a botanical feedstock (e.g. *cannabis*) using a condensable gas solvent.

In any of the embodiments disclosed herein, the solvent may be a condensable gas. Optionally, the solvent comprises carbon dioxide ($CO_2$). Use of $CO_2$ as a solvent may have one or more advantages. For example, carbon dioxide extraction may provide relatively pure, solvent-free extracts, e.g. it may leave little or no residue in the extracted compounds. It may also be characterized as an environmentally friendly or 'green' alternative to other solvent-based extraction techniques. Also, the density of $CO_2$ can be altered by varying the pressure and temperature, which may allow for selective extraction of one or more targeted compounds. Also, the low viscosity of supercritical carbon dioxide may allow it to penetrate into the botanical material more easily, while its diffusivity may allow for faster extractions.

Alternatively, the condensable gas solvent may include one or more of a hydrocarbon (such as ethane, propane, butane, cyclopropane, ethane), optionally a haloalkane, xenon, krypton, nitrous oxide, and sulfur hexafluoride. The selection of a particular condensable gas may be influenced by the strain of *cannabis* from which compounds are to be extracted, the particular compound or compounds targeted for preferential extraction, and/or a targeted speed and/or efficiency of the extraction.

As exemplified in FIGS. 1 to 4, apparatus 1000 comprises at least one extraction chamber 100 and at least one cyclonic separator 200. A solvent flow path 300 extends from the extraction chamber to the cyclonic separator. In use, botanical material (e.g. *cannabis*) is exposed to solvent in the extraction chamber, under process conditions that result in one or more compounds (e.g., terpenes) present in the botanical material being dissolved by the solvent and drawn from the botanical material. Solvent containing the dissolved extracted compound(s) is conveyed to the cyclonic separator via the solvent flow path. At the cyclonic separator 200, the extracted compound(s) are disassociated or separated from the solvent, and the extracted compounds may then be collected for use and/or further processing.

Extraction chamber 100 may be any extraction chamber and, optionally, an extraction chamber useable with a condensable gas and optionally, an extraction chamber operable at conditions at which a condensable gas is in a supercritical phase.

Extraction chamber 100 has at least one botanical feedstock port or inlet 110. Botanical feedstock port or inlet 110 is openable to allow a botanical feedstock to be introduced into and/or a botanical feedstock that has been subjected to extraction to be removed from the interior of the extraction chamber. For example, feedstock inlet 110 may comprise a feedstock inlet port with an openable door 112.

In the illustrated schematic example, a single feedstock port 110 is provided at a side of extraction chamber 100. It will be appreciated that in alternative embodiments, two or more ports 110 may be provided (e.g., an inlet port and a used feedstock removal port). Further, the port(s) may be placed elsewhere (e.g., on an upper and/or lower portion of the extraction chamber).

Extraction chamber 100 also has at least one solvent inlet through which solvent (e.g. a condensable gas solvent) may be introduced in to the extraction chamber. In the illustrated schematic example, a single solvent inlet port 120 is downstream of a source solvent. If the solvent is a condensable gas solvent, then port 120 may be downstream of a source of pressurized solvent. Any source of pressurized solvent may be used. For example, a tank 60 of pressurized gas, a pump, or another suitable pressure control device (e.g. a diaphragm compression system). As exemplified, solvent inlet port 120 is shown in communication with solvent pump 50, which is itself in communication with a solvent reservoir (e.g. solvent tank 60).

If solvent is recycled, then as exemplified, a solvent return conduit 40 may be provided through which solvent may be recycled back to the extraction chamber (as discussed further below), either directly or through tank 60.

It will be appreciated that in alternative embodiments, two or more solvent inlets may be provided. For example, the downstream end of return conduit 40 may be in communication with tank 60 or may be conveyed directly to extraction chamber 100 (such as by a separate pump).

During operation of the extractor, solvent pump 50 or another suitable pressure control device (e.g. a diaphragm compression system) may be used in controlling process conditions of the solvent in the extraction chamber. For example, solvent pump 50 may be used to control the pressure of solvent within the extraction chamber, which may assist in bringing solvent to a desired phase (e.g. liquid, supercritical fluid) and/or a desired density, and in maintaining solvent at a desired phase and/or desired density. Preferably, the pressure control system allows the extraction chamber pressure to be selectively varied across an operational range of about ambient to about 5,000 psi, and may be from 800 to 5,000 psi, 1,000 to 4,000 psi, 1,500 to 3,500 psi and 2,000 psi to 3,000 psi. Examples of operating pressure ranges of extraction chamber 100 may be from 800 to 1,000 psi, from 1,000 to 1,200 psi, from 1,200 to 1,400 psi, from 1,400 to 1,800 psi, from 1,800 to 2,000 psi, or from 2,000 to 4,000 psi.

Optionally, as exemplified, extraction chamber 100 may have one or more heat transfer members 135 that may be used to control the temperature of the interior of the extraction chamber by adding thermal energy to and/or removing thermal energy from, the interior of the chamber. For example, heat transfer member 135 may include a heating jacket through which fluid may be circulated to raise or lower the temperature of portions of the chamber wall. Alternatively, or additionally, heat transfer member 135 may include electrical heat tracing bonded (e.g. directly bonded) to an exterior surface of the extraction chamber. As the extractor vessel may need to be heated and cooled to maintain desired operating conditions, the use of electrical heat tracing would require a cooling system if the extractor is also to be cooled.

During operation of the extractor, heat transfer member 135 may be used in controlling process conditions of e.g. solvent in the extraction chamber. For example, heat transfer member 135 may be used to control the temperature of solvent within the extraction chamber, which may assist in bringing solvent to a desired phase (e.g. liquid, supercritical fluid) and/or a desired density, and in maintaining the solvent at a desired phase and/or desired density. Preferably, heat transfer member 135 may allow the extraction chamber temperature to be selectively varied across an operational range of from about −20° C. to about 110° C. and may be from 0 to 90° C., from 20 to 70° C., and from 20-50° C. Examples of operating temperature ranges of extraction chamber 100 may be from −20° C. to 0° C., from 0° C. to 20° C., from 20° C. to 50° C., from 50° C. to 110° C., from 50 to 70° C., or from 70 to 90° C.

It will be appreciated that if the solvent is a condensable gas solvent, then the solvent may be introduced into extraction chamber 100 as a liquid or in a supercritical phase, or may be changed to be a liquid or at a supercritical phase once introduced into the extraction chamber. For example, if the solvent is introduced as a liquid, it may be subjected to conditions in the extraction chamber which result in the solvent transitioning to a supercritical phase.

An advantage of providing an extraction chamber that can be operated at temperatures, e.g., from about −20° C. to about 110° C. and at, e.g., pressures of up to about 4,000 psi it that such an extraction chamber may allow the flexibility to run extractions across the most variable regions of the phase space of $CO_2$, spanning gas, liquid, and supercritical.

In some embodiments, heat transfer member 135 may also be used to control the temperature of botanical feedstock positioned in the extraction chamber. For example, after being introduced into the chamber, botanical material may be cooled until some, substantially all, or all of the water in the botanical material transitions to a solid phase (i.e. the material may be frozen or partially frozen). For example, at least 50%, 60%, 70%, 80% or 90% of the water in the feedstock may be in a solid phase. Alternatively, botanical material introduced into the extraction chamber in a frozen or partially frozen state may be maintained in such a state using heat transfer member 135.

An advantage of freezing the botanical material is that this may impede or prevent water in the botanical material from being dissolved by the solvent. This may result in a more 'complete' extract being obtained, and may also improve the speed and/or efficiency of the solvent extraction.

Another advantage of freezing the botanical material is that this may reduce or obviate the need to desiccate the material prior to extraction. This may be particularly advantageous for extracting compounds (e.g., terpenes) from a *cannabis* feedstock. For example, this may allow *cannabis* to be harvested and introduced into the extraction chamber without undergoing a drying process to remove moisture from the *cannabis* feedstock, or only undergoing an abbreviated drying process.

For example, *cannabis* having a moisture content above about 12%, or above about 9%, may be characterized as being 'fresh' or 'undried' *cannabis*. As drying *cannabis* may be a relatively lengthy process, and may involve a dedicated drying room or other specialized drying apparatus, the ability to extract compounds from 'fresh' *cannabis* may result in overall process efficiencies, reduced process time, and/or cost savings.

Also, one or more compounds typically present in *cannabis* may be lost, damaged, or otherwise adversely affected during a typical drying process. For example, volatile terpenes and aldehydes may be considered particularly susceptible to loss during drying. Accordingly, extractions performed with an undried feedstock or even a feedstock that has only partially been dried may facilitate a greater extraction and recovery of these compounds.

As exemplified in FIG. 1, a conduit 30 provides a flow path for solvent to flow from the extraction chamber 100 to the cyclonic separator 200. As exemplified, conduit 30 extends between a solvent outlet 130 of the extraction chamber 100 and a fluid inlet 210 of the cyclonic separator 200.

As exemplified, one or more heat transfer members 35 may be provided along at least a portion of the solvent flow path between solvent outlet 130 of the extraction chamber 100 and a fluid inlet 210 of the cyclonic separator 200. The heat transfer member 35 may be any heat transfer member used to transfer heat between the member 35 and the solvent in the flow path. Accordingly, the heat transfer member 35 may be used to control the temperature of solvent by adding thermal energy to, or removing thermal energy from, solvent flowing through the conduit.

Typically, heat is added to the solvent in the flow path to convert the solvent to a supercritical or gaseous phase. When the heat transfer member 35 is used to heat solvent flowing through the solvent flow path, the location(s) at which a heat transfer device is provided may be characterized as a 'heating zone'.

It will be appreciated that any heat transfer member 35 may be used. The heat transfer member may be a heat exchanger, such as a cross flow heat exchanger or an in-line heat transfer member. For example, a heating jacket may be provided on part of the conduit 30. Alternatively, or additionally, heat transfer member 35 may include electrical heat tracing bonded (e.g. directly bonded) to an exterior surface of the conduit.

It will be appreciated that heat transfer member 35 may be located at any location along conduit 30. Optionally, the heat transfer member 35 may be located towards the downstream end of conduit 30, such as one or more of proximate fluid inlet 210 of the cyclonic separator, as part of fluid inlet 210 of the cyclonic separator, immediately upstream of fluid inlet 210 of the cyclonic separator, and immediately upstream of a sonic flow nozzle. An advantage of positioning the heat transfer member 35 closer to the entrance to the cyclone separator is that the solvent may be maintained in a liquid or supercritical phase for most or all of the length of conduit 30. Liquid and supercritical states have better solubilization characteristics than gaseous solvent. Further, when the solvent converts to the gaseous state, extracted botanical elements, which may be oily, may separate from the solvent and may foul conduit 30 and other parts of the flow path. Accordingly, maintaining the solvent in a liquid or supercritical phase for longer may reduce fouling of the flow path.

It will be appreciated that one or more control valves or other flow control devices may be positioned in the solvent flow path to assist in controlling process conditions, e.g., flow rate and/or the temperature of the solvent entering the cyclonic separator, between the extraction chamber 100 and the cyclonic separator 200. Additionally, or alternatively, one or more sensors, such as temperature sensors (e.g. a thermocouple, resistive thermal device, and the like) and/or pressure sensors (e.g. a quartz-based sensor, electrical resonating diaphragm, and the like) may be positioned along the solvent flow path, e.g. to provide data to a process control system, such as a SCADA control system or the like.

Cyclone separator has a tangential fluid inlet 210. Any tangential cyclone inlet may be used. Accordingly, fluid inlet 210 may be positioned and constructed in any manner suitable for directing solvent tangentially into cyclone chamber 205. Optionally, two or more tangential inlets may be spaced around the circumference of the cyclone chamber, which may facilitate cyclonic rotation of solvent within the cyclone chamber.

Cyclone separator 200 may be any cyclone separator known in the separation arts. As exemplified in FIG. 1, cyclone separator 200 has a fluid inlet 210 and a fluid outlet 220 at the upper end of the cyclone separator 200 and a separated material outlet 230 at the lower end of the cyclone separator 200. In use, solvent may enter the cyclone chamber 205 of FIG. 1 tangentially through the fluid inlet 210, and swirl (e.g. move cyclonically) in the cyclone chamber to promote separation of compounds extracted from the botanical material from the solvent. Solvent from which the compound(s) have been separated may exit the cyclone chamber 205 through a gas outlet 220 provided at an upper end of the cyclone separator 200. The separated compound(s) may exit the cyclone chamber 205 through the separated material outlet 230 provided at a lower end of the cyclone separator.

Optionally, as exemplified in FIG. 1, apparatus 1000 may also include a nozzle 300 positioned adjacent (e.g., immediately upstream of or as part of) tangential fluid inlet 210 of cyclone chamber 205. In the illustrated example of FIG. 2, tangential fluid inlet 210 is positioned directly downstream of (e.g., abutting) an outlet 320 of nozzle 300. Such an arrangement may allow solvent exiting flow nozzle 300 to be directly tangentially introduced into the cyclonic tangential fluid inlet 210 and/or the cyclone chamber 205. In some embodiments, the cyclonic tangential fluid inlet 210 may comprise the nozzle 300.

Optionally, nozzle 300 accelerates the solvent passing therethrough (such as a convergent nozzle) and may be a sonic flow nozzle (such as a converging-diverging nozzle).

Figure 3:
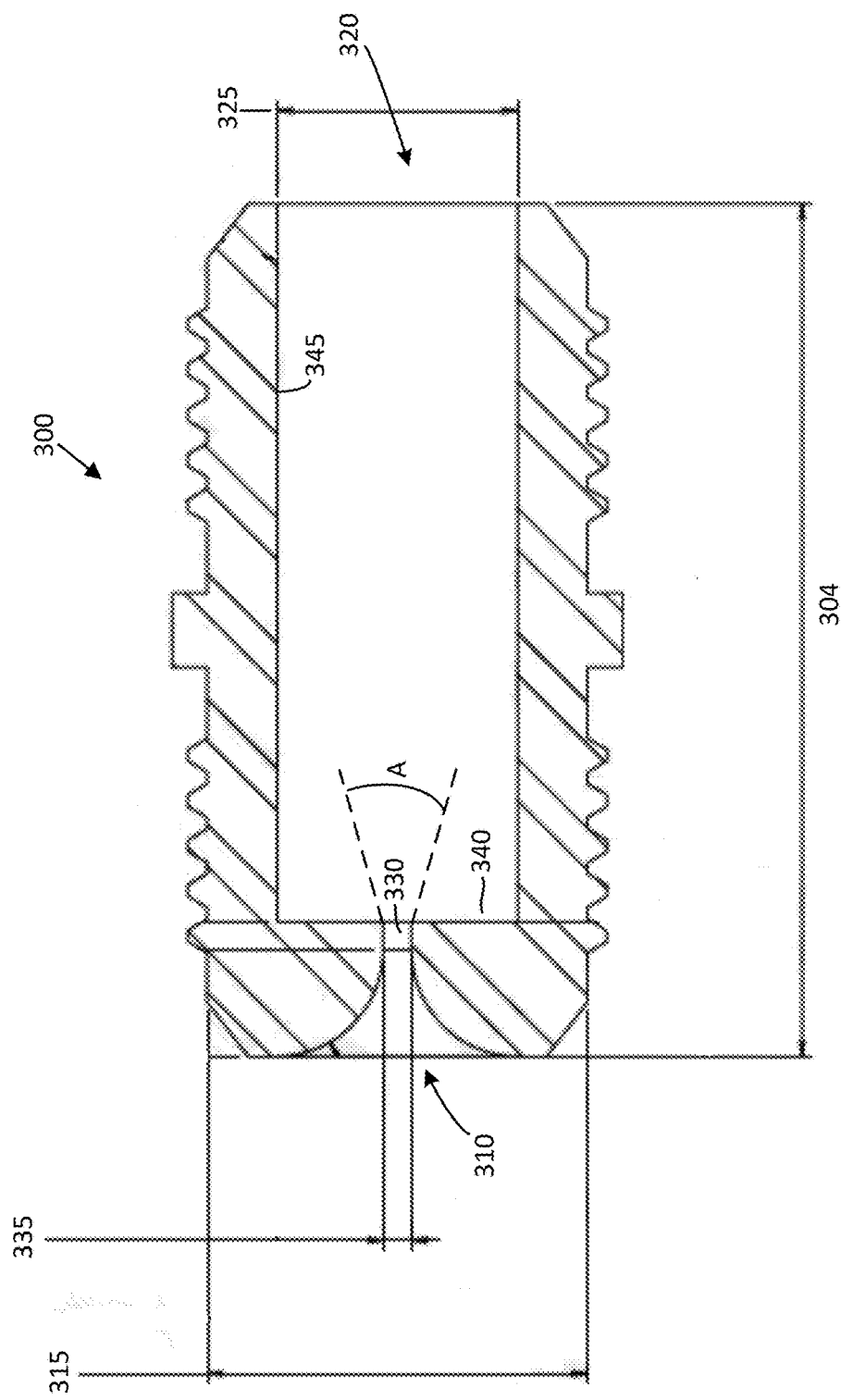
FIG. 3 is a cross-section view of the sonic flow nozzle of the apparatus of FIG. 1.
Figure 4:
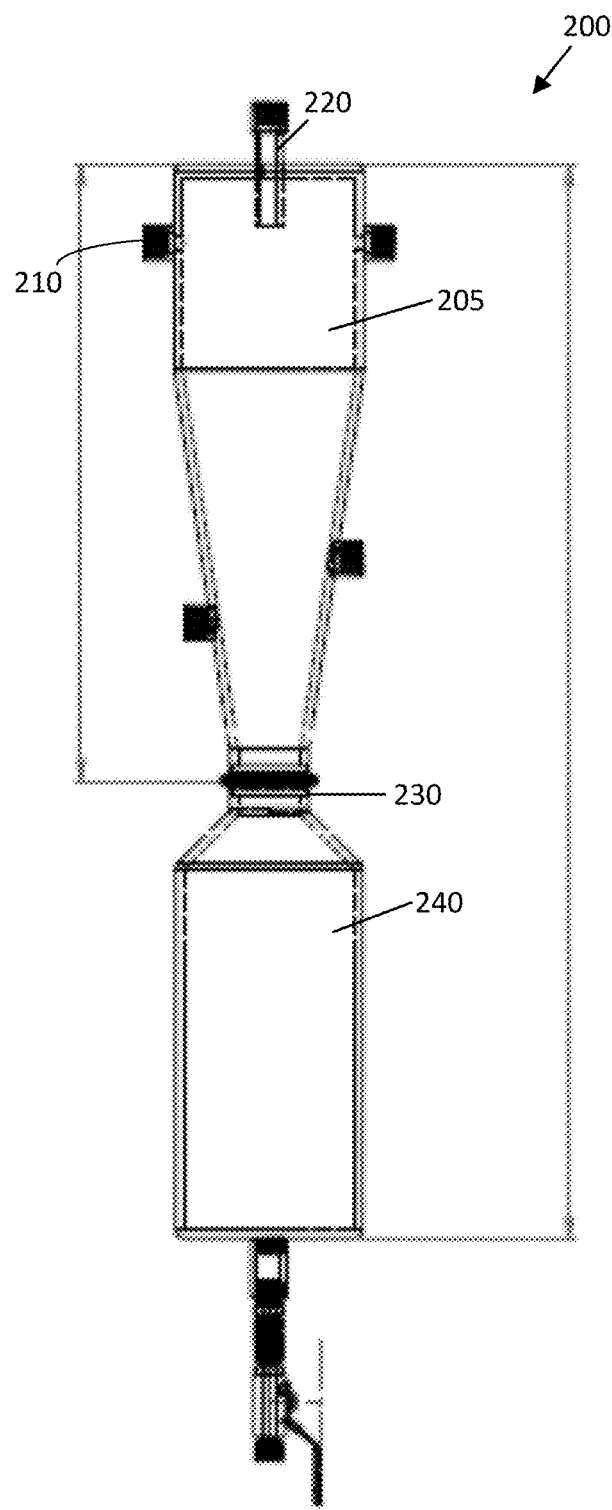
FIG. 4 is a cross-section view of the cyclonic separator of the apparatus of FIG. 1.

In alternative embodiments, flow nozzle 300 may comprise an orifice plate. A cross-section of an example of a nozzle 300 is illustrated in FIG. 3. As exemplified, nozzle 300 has an inlet end 310 and an outlet end 320. The internal diameter of the nozzle narrows in the direction of flow, from an inlet diameter 315 at the inlet end to a smaller diameter 335 at the nozzle throat 330. Downstream of the throat 330, the diameter increases. As exemplified, the wall 340 at the outlet of the throat 330 is generally transverse to the direction of flow through the nozzle. The diameter of the nozzle therefore immediately increases to a diameter 325 which is larger than throat diameter 335 and may be about the same as inlet diameter 315. It will be appreciated that wall 340 may extend in the direction of flow at an angle of less than 90° (which is exemplified in FIG. 3). Fluid exiting throat 330 expands at a dispersion angle A of from 90° to 70°, from 85° to 70°, from 80° to 70°, or from 75° to 70°.

The nozzle 300 may be positioned and configured such that fluid exiting outlet 320 of nozzle 300 may enter into the cyclone chamber without impinging on an interior wall 345 of the downstream part of nozzle 300 and/or tangential fluid inlet 210. Alternatively, fluid may only impinge on a downstream part of the interior wall 345 of the downstream part of nozzle 300 and/or the tangential fluid inlet 210. For example, the dispersion angle A may be selected such that fluid exiting nozzle 320 will not impinge upon the wall of the tangential inlet. It will be appreciated that wall 345 may define part or all of the tangential inlet. An advantage of design is that separation of compound(s) from the solvent in the flow stream downstream of throat 330 may reduce or prevent an accumulation of separated compounds within the nozzle and/or tangential inlet.

In use, the apparatus is preferably operated under process conditions in which the nozzle operates in a 'choked' state. For example, a ratio of the pressure of the fluid entering the nozzle inlet (which may be referred to as the "nozzle inlet pressure" or "upstream pressure") and the pressure of the fluid exiting the nozzle outlet (which may be referred to as the "nozzle outlet pressure" or "downstream pressure") is preferably greater than 1.4 and may be from 1.4:1 to 14.2:1, from 1.4:1 to 7.2:1, from 4.2:1 to 14.2:1. Examples of operating ranges that may be used are 1.4:1 to 4.2:1, from 4.2:1 to 7.2:1, from 7.2:1 to 14.2:1. An advantage of operating the flow nozzle under 'choked' conditions is that the mass flowrate through the nozzle is only influenced by the upstream pressure and upstream temperature (i.e. density) of fluid entering the nozzle. Accordingly, upstream pressure disturbances (e.g. pressure pulsation due to pumps, flow fluctuations as a result of extraction, etc.) may be inhibited or prevented from moving downstream past the nozzle 300 and into the cyclonic separator, and thus may be inhibited or prevented from causing undesirable pulsations and/or vortex flow instabilities during the decompression and/or separation that occurs in the cyclonic separator.

Figure 8:
FIG. 8 is an image of a foamed extract exiting a cyclone chamber wherein a sonic flow nozzle is not utilized; and, FIG. 9 is an image of an extract obtained from a cyclone separator wherein a sonic flow nozzle was utilized.

By providing a sonic flow nozzle 300, solvent passing through the nozzle may enter the cyclone chamber at sonic or supersonic velocity. An advantage of this design is that the radial acceleration resulting from the solvent being rotated in the cyclone chamber while travelling at sonic or supersonic velocities may be more effective at promoting disassociation (i.e. separation) of extracted compound(s) from the solvent, as compared to sub-sonic flow. For example, in typical gas-liquid cyclonic separators (e.g. with sub-sonic fluid injection), there may be significant 'carry over' of entrained product exiting the separator along with the solvent exiting the cyclone outlet, which may lead to fouling of e.g. low pressure piping and compression pumps positioned downstream of the cyclone gas outlet. Further, the separated material tends to be foamed with entrained solvent as exemplified in FIG. 8.

Optionally, as exemplified in FIG. 1, the cyclone separator 200 includes a temperature control system, which in the illustrated example is shown as a heat transfer member 235 such as a heat jacket 235. Alternatively, or additionally, heat transfer member 235 may include electrical heat tracing bonded (e.g. directly bonded) to an exterior surface of the cyclone separator 200. Heating jacket 235 may be used to convey thermal energy to the interior wall 215 of the cyclone chamber 205. Heating the cyclone chamber may have one or more advantages. For example, compounds separated from the solvent in the cyclone separator that come into contact with the interior wall of the cyclone separator may thereby be heated, which may reduce the viscosity of the separated compounds. An advantage of reducing the viscosity of the separated compounds is that they may more easily and/or rapidly flow down the walls of the cyclone separator (due to gravity) to a collection chamber, such as collection chamber 240.

Separated material exiting separated material outlet 230 may be collected in any manner known in the separation arts. As exemplified in FIG. 1, a separated material collection chamber 240 in communication with the separated materials outlet 230 of cyclonic separator 200 may be provided to receive compounds disassociated (i.e. separated) from solvent entering fluid inlet 210 of the cyclonic separator 200.

Preferably, the separated material collection chamber 240 is removable from the cyclonic separator 200. Providing a detachable separated material collection chamber 240 may allow a user to transport (e.g. carry) the collected separated material (e.g. compound(s) extracted from *cannabis*) to another location for emptying and/or further processing, without needing to carry or move the cyclonic separator 200. Preferably, the separated material collection chamber 240 is removable as a closed module, which may help prevent the extracted compounds from spilling out of the separated material collection chamber 240 during transport.

Alternatively, the separated materials outlet 230 may be in flow communication with (connected or removably connected to) a conduit which transports the separated compound(s) to, e.g., another piece of equipment for further processing.

As exemplified in FIG. 1, a gas return conduit 40 may optionally be provided between a gas outlet 220 of the cyclone separator and a solvent inlet 120 to the extraction chamber 100. An advantage of this design is that it may allow the gas solvent to be recycled to the extraction chamber 100 after extracted compounds have been disassociated from the solvent in the cyclone chamber. This may be characterized as a 'closed-loop' system. Optionally, one or more gas pumps 55 or other flow control devices may be provided to re-pressurize the solvent prior to its reintroduction to the extraction chamber and/or a storage tank, such as tank 60. An advantage of recycling solvent (e.g. $CO_2$) is that such a closed loop system may reduce solvent usage, and may therefore be characterized as a low consumption, environmentally friendly, and/or 'green' process. Alternatively, such a solvent recycling system may not be provided, and solvent exiting the cyclone separator may be expelled or stored, without being recycled back to the extraction chamber.

In one embodiment, the apparatus includes both a heat transfer member 35 and a nozzle 330. The heat transfer member 35 is located immediately upstream from nozzle 300. Accordingly, solvent entering the nozzle 300 may be gaseous. An advantage of this design is that the solvent may be maintained in a liquid or supercritical phase until just before it enters nozzle 300 and may then enter the cyclone chamber with no or only minimal impingement on the wall of the flow path downstream of nozzle 300, thereby limiting or preventing the fouling of the flow path downstream of nozzle 300.

General Description of a Method for Extracting Compounds from Botanical Material Using a Condensable Gas Solvent The flowing is a description of a method for extraction which may be used by itself or in combination with one or more of the other features disclosed herein including the use of any of the features of the apparatus and/or and any of the methods disclosed herein.

Figure 6:
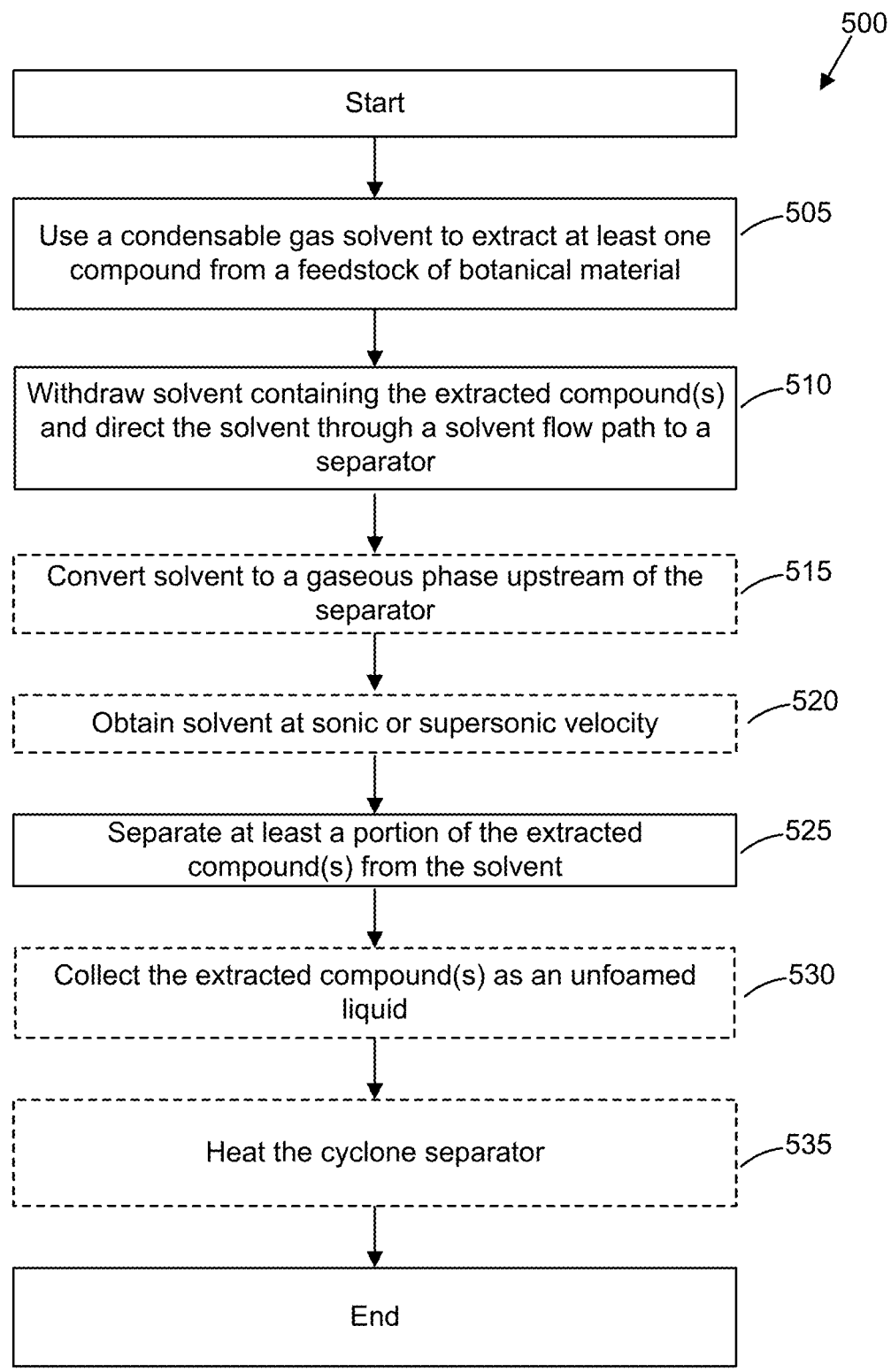
FIG. 6 is a simplified process flow diagram for a method for extracting compounds from botanical material using a condensable gas solvent in accordance with one embodiment.

Referring to FIG. 6, there is illustrated a method 500 for extracting compounds from botanical material using a condensable gas solvent. Method 500 may be performed using apparatus 1000 or any other suitable apparatus for the extraction of compounds from a botanical material. FIG. 6 exemplifies a method in which a single extraction operation is conducted and a single cyclone separator is used. As discussed herein, the same feedstock may be subjected to two or more extraction operations, which may be conducted at the same conditions or at different conditions, and each extraction operation may use the same solvent or a different solvent. Further, as also discussed herein, an extraction operation or a series of extraction operations, may use two or more cyclone separators. It will be understood that the method exemplified in FIG. 6, with any one or more of the optional steps, may be used with a method employing multiple extraction steps and/or multiple cyclone separators.

At 505, in an extraction chamber, such as extraction chamber 100, a condensable gas solvent is used to extract at least one compound from a feedstock of botanical material. For example, the botanical material (e.g. *cannabis*) may be introduced into chamber 100 through a feedstock inlet 110 provided at the end of chamber 100. Once the botanical material has been introduced and the feedstock inlet closed, a condensable gas solvent (e.g. carbon dioxide) may be introduced into the extraction chamber, and process conditions within the extraction chamber (pressure, temperature, etc.) may be controlled so that the botanical material is exposed to solvent at a predetermined state (phase, density, temperature, pressure, etc.) for a predetermined time, during which one or more compounds present in the botanical material are dissolved by the solvent and extracted from the botanical material. It will be appreciated that the condensable gas may be introduced into chamber 100 at the predetermined state and the conditions in chamber 100 may maintain the condensable gas in the predetermined state. The extraction chamber may be at any pressure and temperature discussed herein The condensable gas may be used to extract one or more compounds from the feedstock. Optionally, if the botanical material is *cannabis*, compounds extracted by the solvent may include one or more of an aliphatic aldehyde (e.g. nerol, geraniol, octanal, decanal), a terpene (e.g. limonene, pinenes, ocimenes), and a cannabinoid.

Optionally, in any embodiment, a fresh feedstock of *cannabis* may be obtained and introduced into extraction chamber 100. For example, *cannabis* may be harvested and introduced into the extraction chamber without undergoing a drying process to remove moisture from the *cannabis* feedstock.

Optionally, in any embodiment, a *cannabis* feedstock (fresh or dried) may be comminuted prior to being introduced into the extraction chamber in order to increase the surface area of the botanical material.

Optionally, in any embodiment, a feedstock of fresh *cannabis* may be provided to an extraction chamber where water in the feedstock is in a solid phase (which may be characterized as frozen or partially-frozen *cannabis*). Alternatively, unfrozen *cannabis* may be provided to extraction chamber 100, and the temperature of the extraction chamber 100 brought to and/or maintained at a temperature below the freezing point of water (e.g. using heat transfer member 135) until water in the feedstock transitions to the solid phase.

Optionally, in any embodiment, condensable gas solvent in the extraction chamber may be brought to and/or maintained in at least one of a liquid phase and a supercritical phase, and used to extract at least one compound from the *cannabis* while in a liquid and/or supercritical phase. For example, process conditions within the extraction chamber (pressure, temperature, etc.) may be controlled so that solvent in a liquid phase and/or in a supercritical phase contacts the botanical feedstock for a predetermined time, during which one or more compounds present in the feedstock are dissolved by the solvent and extracted from the feedstock.

At 510, solvent containing the dissolved or extracted one or more compounds is withdrawn from the extraction chamber and the solvent (which may be characterized as a 'solvent stream') is then conveyed through a solvent flow path to a separator. For example, solvent may be withdrawn from extraction chamber 100 via solvent outlet port 130, and conveyed to fluid inlet 210 of cyclonic separator 200 through solvent conduit 30.

Optionally, at 515, at least some solvent may be converted to a gaseous phase upstream of the cyclone chamber. For example, the solvent stream may be heated prior to entering the separator. For example, heating jacket 35 or another heating member may be used to heat solvent as it passes through the solvent flow path. Heating the solvent may cause some, a substantial portion of, or all (e.g., more than 50%, 60%, 70%, 80%, or 90%) of the solvent in a liquid phase to transition to a gaseous phase and/or to a supercritical phase.

Alternatively, or additionally, the pressure of the solvent stream upstream of the cyclone chamber may be lowered, e.g. via one or more control valves positioned in the solvent flow path. Reducing the pressure of the solvent stream may cause some, a substantial portion of, or all (e.g., more than 50%, 60%, 70%, 80%, or 90%) of any liquid solvent to transition to a supercritical and/or gaseous phase. Also, reducing the pressure may cause some, a substantial portion of, or all (e.g., more than 50%, 60%, 70%, 80%, or 90%) of any supercritical solvent to transition to a gaseous phase.

Optionally, at 520, solvent traveling at sonic or supersonic velocity may be obtained. For example, a sonic flow nozzle 300 may be positioned in the solvent flow path upstream of the fluid inlet to the cyclone chamber, and the nozzle inlet pressure, nozzle outlet pressure, and/or nozzle backpressure may be adjusted so that most or substantially all of the solvent exits the sonic flow nozzle at sonic or supersonic velocity. Advantageously, this may allow solvent to be directed into a cyclone chamber at sonic or supersonic velocity. Optionally, the solvent may be heated immediately upstream of the nozzle 300.

At 525, some, or preferably most, or more preferably substantially all of the extracted compound(s) is separated from the solvent. For example, the solvent stream may be directed into a cyclonic separator, such as cyclonic separator 200.

Preferably, solvent is introduced tangentially into a cyclone separator, e.g. via a tangential cyclone inlet, such as tangential cyclone inlet 210. Optionally, if a nozzle 300 is utilized, the nozzle may be positioned immediately upstream of a tangential cyclone inlet or nozzle 300 may be the tangential cyclone inlet. Accordingly, solvent may be introduced directly into the cyclone separator, i.e. without being directed through a conduit or the like between a nozzle outlet and the cyclone separator. For example, the outlet of the nozzle 300 may be positioned adjacent the cyclone separator, and solvent exiting the sonic flow nozzle may be directed so as to avoid contacting sidewalls of a conduit downstream of the nozzle 300 and/or an inlet port of the cyclone separator.

As another example, the outlet of the sonic flow nozzle may be positioned at an inlet port of the cyclone separator, and solvent exiting the sonic flow nozzle may be conveyed immediately into the cyclone separator so as to avoid contacting the inlet port of the cyclone separator.

An advantage of introducing solvent directly into the cyclone separator when the solvent has been converted to a gaseous state is that it may inhibit fouling of the sidewalls of a conduit downstream of the nozzle 300 by an extract that is liberated from the solvent when it becomes gaseous.

Figure 9:
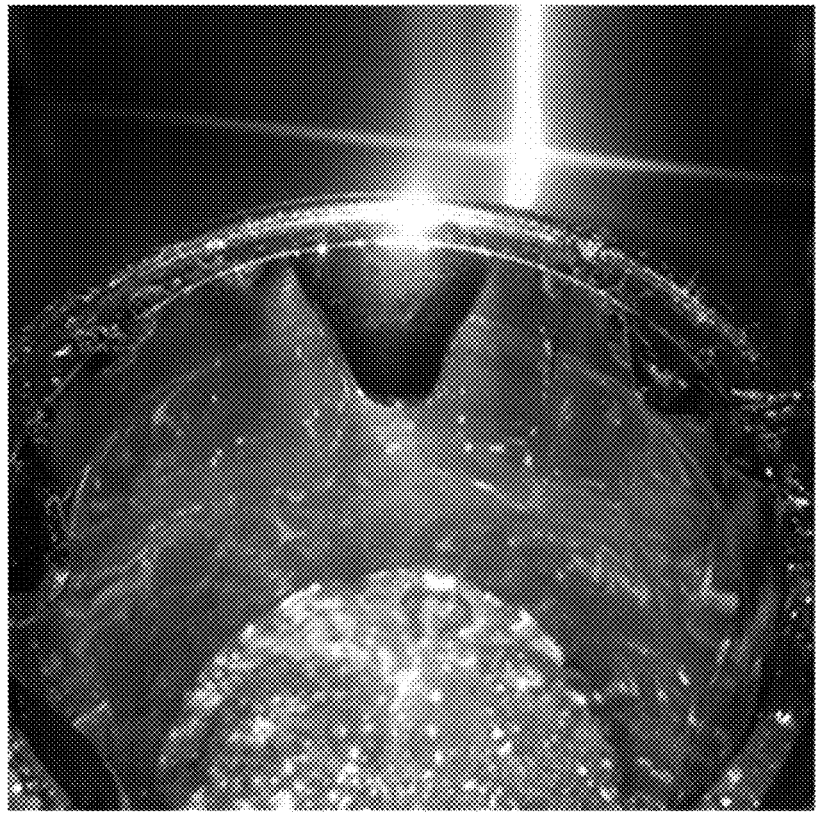

Optionally, at 530, some, or preferably most, or more preferably substantially all of the at least one compound dissolved in the solvent may be separated in the cyclone separator and collected as an unfoamed liquid as exemplified in FIG. 9. For example, if the botanical material is *cannabis*, compounds separated from the solvent in the cyclone separator may include one or more of an aliphatic aldehyde, a terpene, and a cannabinoid.

An advantage of collecting the separated at least one compound as an unformed liquid is that the collected liquid may be easier to work with and/or easier to post-process.

Optionally, at 535, the cyclone separator may be heated. For example, a temperature control system such as heating jacket 235 or the like may be used to convey thermal energy to the interior wall of the cyclone separator during operation of the cyclone separator. The cyclone separator may be heated to raise the temperature of the cyclone chamber to a predetermined temperature prior to the separation operation. Alternately or in addition, the temperature control system may be used to maintain the temperature of the cyclone chamber at a predetermined temperature during operation. For example, if a sonic flow nozzle is utilized, the expansion of the solvent may cool the solvent stream which enters the cyclone chamber. The temperature control system may partially or fully counter the cooling effect of the flow through a sonic flow nozzle and may therefore enable the cyclone separator to operate at a design temperature or temperature range. Thus, compounds separated from the solvent in the cyclone separator may thereby be heated or maintained at a design temperature or temperature range, which may reduce the viscosity of the separated compounds. An advantage of reducing the viscosity of the separated compounds is that they may more easily and/or rapidly flow down the walls of the cyclone separator (due to gravity) to a collection chamber, such as collection chamber 240.

Figure 5:
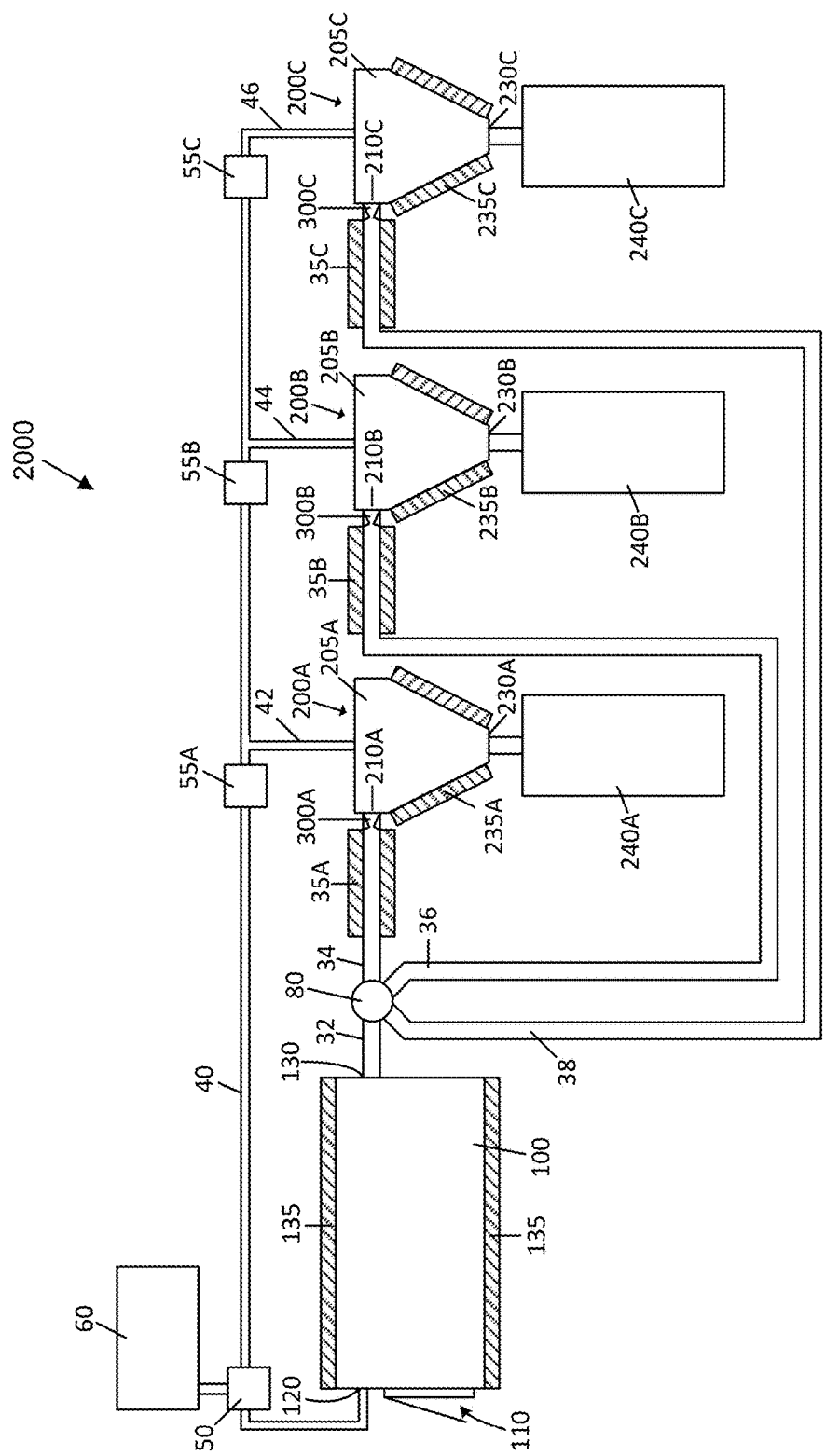
FIG. 5 is a schematic view of apparatus for the extraction of compounds from a botanical material in accordance with another embodiment.

Apparatus for the Extraction of Compounds from Botanical Material with Multiple Cyclonic Separation Stages Referring to FIG. 5, an exemplary embodiment of another apparatus for the extraction of compounds from botanical material is shown generally as 2000. Elements having similar structure and/or performing similar function as those in the example apparatus illustrated in FIGS. 1 to 4 are numbered similarly, and will not be discussed further. As exemplified therein, an extraction and separation operation may use two or more cyclone separators.

As exemplified in FIG. 5, apparatus 2000 includes an extraction chamber 100, a first cyclonic separator 200A, a second cyclonic separator 200B, and a third cyclonic separator 200C. While in the illustrated example three cyclonic separators are shown, in alternative embodiments apparatus 2000 may have only two cyclonic separators, or four or more cyclonic separators may be provided.

Providing an apparatus 2000 with two or more cyclonic separators in parallel may have one or more advantages. For example, each cyclone separator may be configured to disassociate different compounds from a solvent flow. For example, different cyclone separators may be configured to induce different rotational velocities. Higher rotational velocity may be used to separate smaller droplets of liquid or smaller particles containing higher molecular weight compounds which may be separated from a flow stream of solvent in a cyclone. Accordingly, a first cyclone separator may produce a lower rate of rotation of solvent which will result in heavier (larger) droplets of liquid or larger heavier particles being separated than in a second stage cyclone operating at a higher rotational speed. However, the velocity in the first cyclone separator may be insufficient to disentrain lighter (smaller) droplets of liquid or lighter compounds. A second downstream cyclone separator may be operated to produce a higher rotational velocity, which may remove the lighter (smaller) droplets of liquid or lighter compounds. Providing the ability to selectively direct solvent from the extraction chamber to one of two or more cyclonic separators, which may be in series, may facilitate a more complete disassociation of extracted compound(s) from solvent, as solvent containing particular compound(s) can be directed to a separator best suited to disassociate that compound(s). For example, the solvent stream may be sequentially directed though the two or more cyclones (e.g., they may be operated in series). Alternately, different extraction operations may be conducted to selectively remove certain compounds from a feedstock. Therefore, one extraction operation may produce a solvent having heavier compounds and a second extraction operation may produce a solvent having lighter compounds. The solvent from each extraction operation may be directed to a differently configured cyclone (e.g., each cyclone may be configured to separate compounds targeted by a particular extraction operation).

Returning to FIG. 5, in use, botanical material (e.g. *cannabis*) may be exposed to solvent in the extraction chamber 100 under a first set of process conditions to preferentially extract a first set of one or more compounds present in the botanical material from the botanical material. Solvent containing the first extracted compound(s) may be conveyed to the first cyclonic separator 200A, where the first extracted compound(s) are disassociated from the solvent. Subsequently, the botanical material may be exposed to the same or a different solvent in the extraction chamber 100 under a second set of process conditions to preferentially extract a second set of one or more compounds from the botanical material. Solvent containing the second extracted compound(s) may then be conveyed to the second cyclonic separator 200B, where the second extracted compound(s) are disassociated from the solvent. Optionally, the botanical material may subsequently be exposed to solvent in the extraction chamber 100 under a third set of process conditions to preferentially extract a third set of one or more compounds from the botanical material. Solvent containing the third extracted compound(s) may then be conveyed to the third cyclonic separator 200C, where the third extracted compound(s) are disassociated from the solvent.

Preferably, each cyclonic separator may be configured based on the extracted compound(s) expected to be in the solvent flow, which may result in a more thorough and/or efficient disassociation or separation of the compounds from the solvent. For example, if a first set of process conditions of the extractor is designed to preferentially target one or more high-molecular weight compounds for extraction, the first cyclonic separator may be configured to optimize the removal of higher molecular weight compounds from solvent. Similarly, if a second set of process conditions of the extractor is designed to preferentially target one or more lower-molecular weight compounds for extraction, the second cyclonic separator may be configured to optimize removal of lower molecular weight compounds from solvent. For example, during separation, solvent in cyclone chamber 205A of cyclone separator 200A may rotate at a first speed, and solvent in cyclone chamber 205B of cyclone separator 200B may rotate at a second, different speed.

For example, if the botanical material is *cannabis* and the extraction chamber is operated under a set of process conditions to preferentially extract one or more waxes from the *cannabis*, solvent containing the one or more extracted waxes may be directed to a cyclonic separator that is operated at pressure conditions to separate this class of compounds. For example, under extraction conditions that result in a high $CO_2$ density (which may be any combination of pressure and temperature that results in the $CO_2$ being in a high density state, such as over 0.85 g/cm$^3$), waxes may be solubilized and extracted. Solvent containing the waxes may be directed to one or more separators wherein the $CO_2$ is expanded to drop out the solute and the gaseous $CO_2$ which is obtained may be returned to a compression system and recycled into the extractor.

If the extraction chamber is operated under a set of process conditions to preferentially extract one or more light oils from the *cannabis*, solvent containing the one or more extracted light oils may be directed to a cyclonic separator to expand and deposit the solute and return the decompressed $CO_2$ back to, e.g., a pump for recompression and recycle into the extractor. For example, lighter compounds may be selectively extracted by using the $CO_2$ in a low density supercritical state, for example, the density of the solvent may be between 0.25 to 0.35 g/cm$^3$. Such density conditions may be obtained using a number of combinations of pressure and temperature, with the caveat that the temperature be above the critical temperature of 31.1° C., preferably greater than 33° C. to avoid critical point instabilities.

It will be appreciated that the lighter oils and the waxes may be sequentially extracted. In such a case, the extraction operations are optionally conducted so as to initially extract the lighter molecular weight compounds (e.g., the lighter oils) and to then extract the heavier molecular weight compounds (e.g., the waxes). The solvent from the lighter oil extraction operation may be directed to one or more cyclone separators that operate in parallel and which are designed to separate the lighter oils from the solvent. The solvent from the wax extraction operation may be directed at one or more cyclone separators that operate in parallel and which are designed to separate the waxes from the solvent.

Alternatively, a plurality of cyclone stages may be provided in series, wherein each cyclone stage may comprise one or more cyclone separators operating in parallel. The solvent from each extraction stage may be directed sequentially through the plurality of cyclone stages. In such a case, the first stage cyclone separator(s) may be designed to separate the heavier compounds (e.g., compounds having a heavier molecular weight) and the second stage cyclone separator(s) may be designed to separate the lighter compounds (e.g., compounds having a lighter molecular weight). It will be appreciated that three or more cyclone stages may be employed, each using one or more cyclone separators in parallel, wherein each stage recovers lighter compounds than the previous stage.

In an alternative use of apparatus 2000, botanical material (e.g. *cannabis*) may be exposed to solvent in the extraction chamber 100 under a set of process conditions to extract a relatively large range of compounds, and solvent containing the extracted compound(s) may be conveyed to the first cyclonic separator 200A to preferentially disassociate a first set of compounds from the solvent. Next, while the extraction chamber may still being operated under the same set of process conditions, solvent containing the extracted compound(s) may subsequently be conveyed to the second cyclonic separator 200B to preferentially disassociate a second set of compounds from the solvent.

In the illustrated example, a conduit 32 provides a path for solvent to flow from the extraction chamber 100 to a valve 80. Valve 80 may be used to selectively direct solvent from conduit 32 to first cyclonic separator 200A (via conduit 34), second cyclonic separator 200B (via conduit 36), or third cyclonic separator 200C (via conduit 38). Alternative embodiments may include different solvent flow paths and/or valve configurations. For example, in the illustrated example, conduit 32 is common to the solvent flow paths from the extraction chamber to each cyclonic separator, and may therefore be characterized as a common solvent flow path portion. Alternatively, apparatus 2000 may not have a common solvent flow path portion, e.g. by providing separate dedicated conduits from the extraction chamber to each cyclonic separator, wherein each conduit may have an associated valve to selectively direct solvent flow from the extractor to its respective cyclonic separator.

As with the embodiment of FIGS. 1-4, an optional heat transfer device 35 and/or nozzle 300 may be provided along at least a portion of one or more and optionally each solvent flow path, providing each solvent flow path with a 'heating zone', as discussed above.

It will be appreciated that one or more control valves or other flow control devices may be positioned in the solvent flow paths to assist in controlling process conditions between the extraction chamber 100 and each cyclonic separator 200A, 200B, 200C. Additionally, or alternatively, one or more sensors, such as temperature sensors (e.g. a thermocouple, resistive thermal device, and the like) and/or pressure sensors (e.g. a quartz-based sensor, electrical resonating diaphragm, and the like) may be positioned along the solvent flow path(s), e.g. to provide data to a process control system.

As with the embodiment of FIGS. 1-4, apparatus 2000 may also include flow nozzles 300A, 300B, and 300C positioned adjacent the fluid inlet 210A, 210B, and 210C of each cyclone separator 200A, 200B, 200C, respectively. Preferably, each flow nozzle 300 is configured to allow solvent exiting that flow nozzle to be directly tangentially introduced into its corresponding cyclone chamber. Each flow nozzle 300A, 300B, and 300C may be a sonic flow nozzle, such as a convergent nozzle or a converging-diverging nozzle, or an orifice plate or other nozzle.

As exemplified in FIG. 5, separated material collection chambers 240A, 240B, 240C are shown in communication with the separated materials outlets 230A, 230B, 230C of cyclonic separators 200A, 200B, 200C, respectively, to receive compounds disassociated (i.e. separated) from solvent using each cyclonic separator.

Preferably, each separated material collection chamber 240A, 240B, 240C is removable from its respective cyclonic separator 200A, 200B, 200C (e.g. as a closed module). Alternatively, one or more of the separated materials outlets 230A, 230B, 230C may each be in flow communication with a conduit which transports the separated compound(s) to, e.g., another piece of equipment for further processing.

General Description of Another Method for Extracting Compounds from Botanical Material Using a Condensable Gas Solvent The flowing is a description of a method for extraction which may be used by itself or in combination with one or more of the other features disclosed herein including the use of any of the features of the apparatus and/or and any of the methods disclosed herein. The method may be conducted using a solvent stream obtained from any extraction process.

Figure 7:
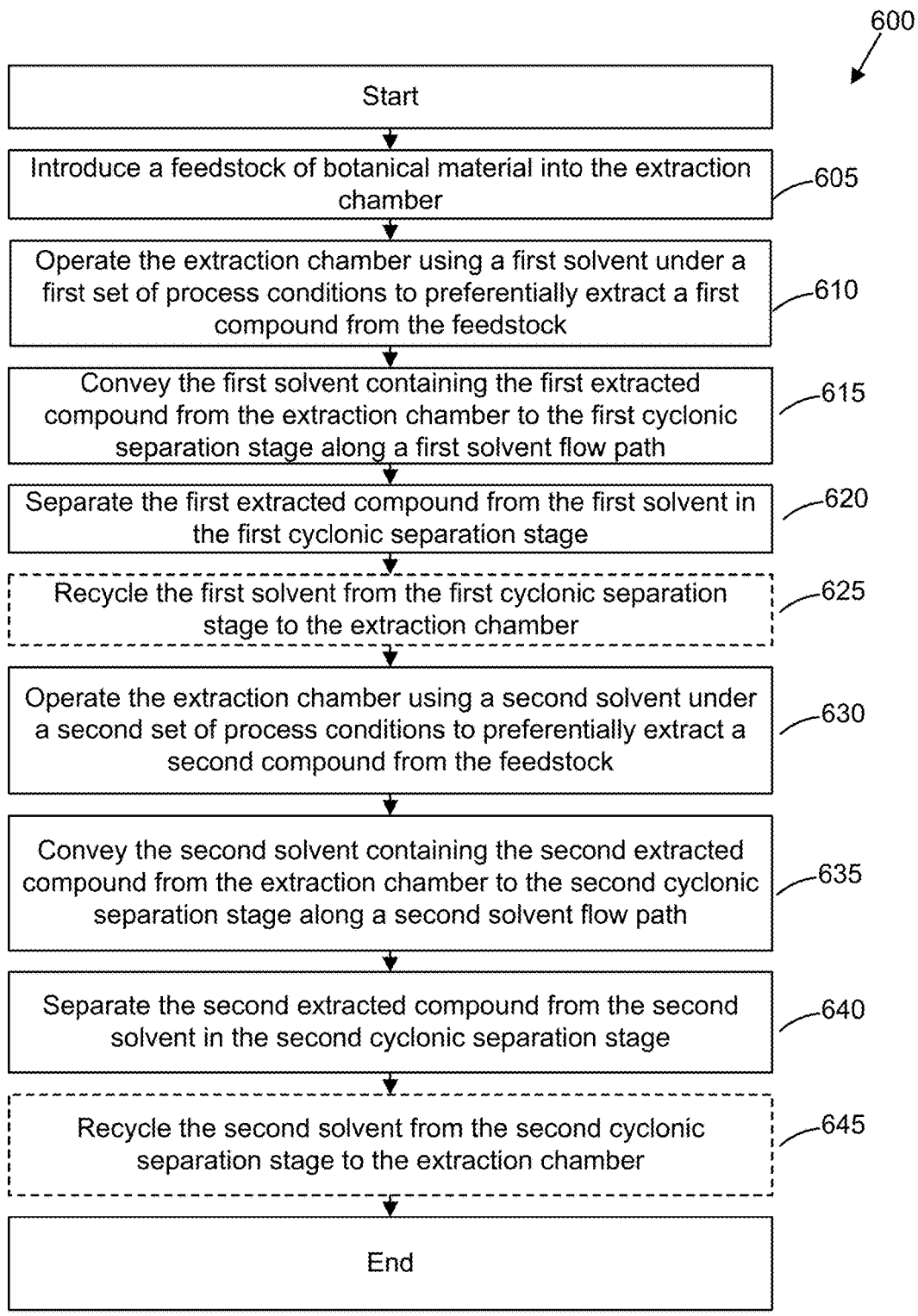
FIG. 7 is a simplified process flow diagram for a method for extracting compounds from botanical material using apparatus comprising an extraction chamber, a first cyclonic separation stage comprising at least one first stage cyclonic separator, and a second cyclonic separation stage comprising at least one second stage cyclonic separator in accordance with one embodiment.

Referring to FIG. 7, there is illustrated a method 600 for extracting compounds from botanical material using apparatus comprising an extraction chamber, a first cyclonic separation stage comprising at least one cyclonic separator, and a second cyclonic separation stage comprising at least one cyclonic separator. Method 600 may be performed using apparatus 2000 or any other suitable apparatus for the extraction of compounds from a botanical material.

At 605, a feedstock of botanical material is introduced to an extraction chamber. For example, a feedstock of *cannabis* may be introduced to extraction chamber 100 through a feedstock inlet 110 of chamber 100. As discussed above, optionally a fresh feedstock of *cannabis* (e.g. *cannabis* having a moisture content of about 9% or about 12%, such as harvested *cannabis* that has not undergone a drying process) may be provided. Optionally, the botanical material may be comminuted prior to being introduced into the extraction chamber in order to increase the surface area of the botanical material. Optionally, the botanical feedstock may be introduced to the extraction chamber in a frozen or partially-frozen state. It will be appreciated that any extraction process and any extraction equipment may be used.

At 610, the extraction chamber is operated using a first solvent under a first set of process conditions to preferentially extract a first compound or compounds from the feedstock. For example, a condensable gas solvent (e.g. carbon dioxide) may be introduced into the extraction chamber, and a first set of process conditions within the extraction chamber (pressure, temperature, etc.) may be controlled so that the botanical material is exposed to first solvent at a predetermined state (phase, density, temperature, pressure, etc.) for a predetermined time, during which a first compound present in the feedstock is preferentially dissolved by the solvent and drawn from the botanical feedstock.

For example, where the botanical feedstock includes *cannabis*, compounds targeted for selective extraction may include one or more aliphatic aldehydes, one or more terpenes, and one or more cannabinoids.

For example, to preferentially extract a lower molecular weight class of compounds using $CO_2$ solvent, the first set of process conditions may operate in the supercritical region of the solvent (e.g. a temperature of about 40° C., and a pressure of about 1200 psi), resulting in a $CO_2$ density that favors low weight compounds.

The first compound or compounds preferentially extracted at 610 may be characterized as a 'target' or 'selected' compound(s) of a first 'targeted' or 'selective' extraction. It will be appreciated that, while the first solvent/set of process conditions are selected so as to preferentially extract the first 'target' compound, one or more additional compounds may nonetheless be extracted from the feedstock during the first selective extraction.

At 615, first solvent containing the first extracted compound is conveyed from the extraction chamber to the first cyclonic separation stage. For example, first solvent may be withdrawn from extraction chamber 100 and directed along conduit 32, valve 80, and conduit 34 to first cyclonic separator 200A.

At 620, some, or preferably most, or more preferably substantially all of the first targeted compound(s) is separated from the first solvent in the first cyclonic separation stage. For example, the first solvent may be directed into a cyclone chamber 205A of the first cyclonic separator, and the first compound may be separated from the first solvent and collected via outlet 230A.

Optionally, at 625, first solvent exiting the first cyclonic separation stage may be recycled to the extraction chamber as discussed previously. For example, first solvent exiting cyclonic separator 200A may be directed through conduits 42 and 40 and re-introduced to extraction chamber 100.

At 630, the extraction chamber is operated using a second solvent under a second set of process conditions to preferentially extract a second compound or compounds from the feedstock. The second solvent may be the same as the first solvent, or a different solvent may be used.

For example, to preferentially extract a higher molecular weight class of compounds using $CO_2$ solvent, the second set of process conditions may also operate in the supercritical region of the solvent, but at a higher pressure (e.g. a temperature of about 40° C., and a pressure of about 3,500 psi), resulting in a $CO_2$ density that approaches that of the liquid state of $CO_2$ and favours higher weight compounds. Thus, higher molecular weight compounds can be effectively solvated and extracted.

Alternative solvents to $CO_2$ can be utilized to favor the extraction of component that are more hydrophilic. For example, using nitrous oxide as a solvent (either on its own or as a co-solvent with $CO_2$) the dipolar nature of the nitrous oxide generates a bias to compounds exhibiting dipolar-like regions on their chemical structure. Alternatively, if one wants to select for highly hydrophobic compounds, condensable hydrocarbons (e.g., propane, ethane) may be used as a solvent, to avoid the extraction of compounds displaying hydrogen bonding or ones containing areas of large charge distribution.

The second compound or compounds preferentially extracted at 630 may be characterized as a 'target' or 'selected' compound(s) of a second 'targeted' or 'selective' extraction. It will be appreciated that, while the second solvent/set of process conditions are selected so as to preferentially extract the second 'target' compound, one or more additional compounds may nonetheless be extracted from the feedstock during the second selective extraction.

At 635, second solvent containing the second extracted compound is conveyed from the extraction chamber to the second cyclonic separation stage. For example, second solvent may be withdrawn from extraction chamber 100 and directed along conduit 32, valve 80, and conduit 36 to second cyclonic separator 200B.

At 640, some, or preferably most, or more preferably substantially all of the second targeted compound(s) is separated from the second solvent in the second cyclonic separation stage. For example, the second solvent may be directed into a cyclone chamber 205B of the second cyclonic separator 200B, and the second compound may be separated from the second solvent and collected via outlet 230B.

Optionally, at 645, second solvent exiting the second cyclonic separation stage may be recycled as discussed previously to the extraction chamber. For example, second solvent exiting cyclonic separator 200B may be directed through conduits 44, 42, and 40 and re-introduced to extraction chamber 100.

It will be appreciated that, as discussed previously, a plurality of cyclone stages may be provided in series, wherein each cyclone stage may comprise one or more cyclone separators operating in parallel and each stage is designed to remove sequentially lighter extracted compounds.

Preferentially extracting different compounds from the feedstock during two or more selective extractions and separations may have one or more advantages. For example, this may provide the ability to fractionate groups of extracted components (e.g. waxes, heavy oils, and light oils) from a single feedstock of botanical material (e.g. *cannabis*), without having to load/unload the extraction chamber (e.g. during a single 'extraction cycle').

Additionally, the cyclonic separation stages may each be configured or 'tuned' to preferentially separate certain selected/targeted compound(s) from solvent. This may allow solvent containing targeted compound(s) to be directed from the extraction chamber to a cyclonic separator best suited to disassociate those compound(s) from solvent. The selective extraction and separation of a greater number of compound(s) may simplify subsequent downstream separations and/or purifications to obtain pure compound isolates.

As used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A method for extracting at least one compound from *cannabis* using a condensable gas solvent, the method consisting essentially of:
   (a) providing *cannabis* to an extraction chamber wherein water in the *cannabis* is in a solid phase;
   (b) extracting at least one compound from the *cannabis* using the condensable gas solvent while maintaining the *cannabis* in a frozen state and obtaining condensable gas solvent containing the at least one extracted compound;
   (c) withdrawing a solvent stream containing the at least one extracted compound from the extraction chamber;
   (d) conveying the condensable gas solvent containing at least one compound extracted from the *cannabis* along a solvent flow path extending from the extraction chamber to a heating zone;
   (e) heating the condensable gas solvent from step (d) and conveying the condensable gas solvent from the heating zone proximate to an inlet of a flow nozzle at conditions at which the condensable gas solvent is at least primarily in a gaseous phase; and,
   (f) directing the condensable gas solvent to a cyclone chamber and operating the cyclone chamber at conditions at which the condensable gas solvent within the cyclone chamber is primarily in a gaseous phase and the at least one compound extracted from the *cannabis* is primarily in a liquid phase,
wherein the condensable gas solvent is selected from the group consisting of carbon dioxide, Xenon, nitrous oxide, ethane, propane, butane, cyclopropane and sulfur hexafluoride.

2. The method of claim 1, wherein the *cannabis* provided to the extraction chamber has a moisture content of at least 9%.

3. The method of claim 2, wherein the *cannabis* provided to the extraction chamber has a moisture content of at least 12%.

4. The method of claim 1, wherein, in step (a) at least 50% of the water in the *cannabis* is in the solid phase.

5. The method of claim 1, wherein the solvent in the extraction chamber is in at least one of a liquid phase and a supercritical phase.

6. The method of claim 1, wherein in step (a), the *cannabis* is introduced into the extraction chamber in an unfrozen state.

7. The method of claim 6, wherein the *cannabis* introduced to the extraction chamber has a moisture content of at least 5%.

8. The method of claim 7, wherein the solvent in the extraction chamber is in a liquid phase.

9. The method of claim 1, wherein the *cannabis* is fresh *cannabis* and in step (a), the fresh *cannabis* is introduced into the extraction chamber.

10. The method of claim 9, wherein the *cannabis* has a moisture content of at least 5% in the extraction chamber.

11. The method of claim 10, wherein the solvent in the extraction chamber is in a liquid phase.

12. The method of claim 1, wherein the at least one compound extracted from the *cannabis* is selected from the group consisting of at least one of an aliphatic aldehyde, a terpene, and a cannabinoid.

13. The method of claim 1, wherein the flow nozzle is a sonic flow nozzle and the solvent in step (e) exits an outlet of the flow nozzle at sonic velocity.

14. The method of claim 1, wherein the temperature of solvent in the extraction chamber is brought to a temperature at or below the freezing point of water, such that at least a portion of the water in the *cannabis* is in a solid phase.

* * * * *